US006331297B1

(12) United States Patent
Allan et al.

(10) Patent No.: US 6,331,297 B1
(45) Date of Patent: Dec. 18, 2001

(54) TICK PHEROMONES AND USES THEREOF

(75) Inventors: Sandra Anne Allan, Gainsville, FL (US); Daniel E. Sonenshine, Virginia Beach, VA (US); Michael John Burridge, Gainesville, FL (US)

(73) Assignees: University of Florida, Gainesville, FL (US); Old Dominion University Research Foundation, Norfolk, VA (US)

( * ) Notice: Subject to any disclaimer, the term of this patent is extended or adjusted under 35 U.S.C. 154(b) by 0 days.

(21) Appl. No.: 09/434,657

(22) Filed: Nov. 5, 1999

Related U.S. Application Data

(60) Provisional application No. 60/107,314, filed on Nov. 6, 1998.

(51) Int. Cl.$^7$ .................................................. A01N 25/00
(52) U.S. Cl. ......................... 424/84; 424/405; 424/406; 424/407; 424/409; 424/93.5; 424/538
(58) Field of Search ................................... 424/405, 406, 424/409, 84, 407, 93.5, 538

(56) References Cited

U.S. PATENT DOCUMENTS

| 229,222 | 6/1880 | Wood . |
| 4,493,161 | 1/1985 | Soloway et al. . |
| 4,883,801 | * 11/1989 | Nanianson ............................ 514/263 |
| 4,884,361 | 12/1989 | Soneshine et al. . |
| 5,149,526 | 9/1992 | Soneenshine et al. . |
| 5,296,227 | 3/1994 | Noraval et al. . |

OTHER PUBLICATIONS

Sonenshine, Daniel E., DeMar Taylor, Gene Corrigan (1985) "Studies to Evaluate the Effectiveness of Sex Pheromone–Impregnated Formulations for Control of Populations of the American Dog Tic, *Dermacentor Variables* (Say) (Acari: Ixodidae)" *Experimental & Applied Acarology* 1:23–34.

Allan, Sandra A., Nicholas Barré, Daniel E. Sonenshine, Michael J. Burridge (1998) "Efficacy of tags impregnated with pheromone and acaricide for control of *Amblyomma variegatum*" *Medical and Veterinary Entomology* 12:141–150.

Norval, R.A.I., Daniel E. Soneshine, Sandra A. Allan, Michael J. Burridge (1966) "Efficacy of pheromone–acaricide–impregnated tail–tag decoys controlling the bont tick, *Amblyomma hebraeun* (Acari: Ixodidae), on cattle in Zimbabwe" *Experimental & Applied Acarology* 20:31–46.

Norval, R.A.I., C.E. Yunker, I.M. Duncan, T. Peter (1991) "Pheromone/acaricide mixtures in the control of the tick *Amblyomma hebraeum*: Effects of acaricides on attraction and attachment" *Experimental & Applied Acarology* 11:233–240.

Uspenskij, I.V. and O. Yu Emelianova (1980) "On the Existence of Pheromone Relations in Ticks of the Genus *Ixodes*" Zool. Zh. 59:699–704. (This article is in Russian but the abstract has been translated to English).

Treverrow, N. L., B.F. Stone and Margaret Cowie (1977) "Aggregation pheromones in 2 Australian hard ticks,*Ixodes holocyclus* and *Aponomma concolor*"*Experientia* 33:680–682.

Martin, Phyllis A. W. and Edward T. Schmidtmann (1988) "Isolation of Aerobic Microbes from *Ixodes scapularis* (Acari: Ixodidae), the Vector of Lyme Disease in the Eastern United States" *J. Economic Entomology* 91(4):1998–2008.

Naumov, R.L. (1990) "Possibility of the Use of Attractants to Control Pasture Ixodid Populations And Ways of Their Search" *Parazitologiya* 24(2):97–101; retreived from EPOQUE, accession no. prev199090121026, XP002134024, abstract.

Dobrotvorskii, A.K. et al. (1989) "The attractant effect of excreta of hungry adults of Ixodes persulcatus P. Sch" retrieved from STN–International, Accession No. 91:27240 CABA XP002134025, abstract.

Dusbabek et al. (1998) "Chemical stability of assembly pheromone of argasid ticks (Ixodoidae: Argasidae)" *Foil Parasitol*. 45(1):62–66; retrieved from STN–International, accession no. 129:37489 CA XP00213426, abstract.

Kalsbeek, V. et al. (1995) "Entomopathogenic fungi associated with Ixodes ricinus ticks" *Experimental and Applied Acarology* 19(1):45–51; retrieved from STN–International, accession no. 95:138422 CABA XP002134027, abstract.

* cited by examiner

*Primary Examiner*—Neil S. Levy
(74) *Attorney, Agent, or Firm*—Saliwanchik, Lloyd & Saliwanchik

(57) ABSTRACT

The subject invention provides materials and methods useful for tick control. The tick control methods of the subject invention are particularly advantageous because they utilize natural chemical signals (phermones) in combination with an acaricide. The use of environmentally friendly phermones makes it possible to use acaricides in a highly selective and efficient manner thereby reducing exposure of the environment to acaricides.

1 Claim, No Drawings

TICK PHEROMONES AND USES THEREOF

CROSS-REFERENCE TO A RELATED APPLICATION

This application claims priority from provisional application U.S. Ser. No. 60/107,314, filed Nov. 6, 1998.

BACKGROUND OF THE INVENTION

Ticks pierce the skin of animals causing infection and are known to spread disease. Protecting livestock from ticks is a major concern of the agriculture industry. Ticks are also known to spread human diseases including Lyme disease.

Over the years, many methods have been developed for controlling tick populations. One common practice used in many countries, including developing countries, is to spray the entire animal with a pesticide. Such spraying operations can pose environmental hazards for the surrounding area as well as health hazards for individuals working near the spraying facility. Using decoys in combination with a pesticide is an attractive alternative to spraying the entire animal. Less pesticide is required since the ticks will be attracted by the decoy to the site where the pesticide is located. Many chemical and visual lures have been used in the past with varying degrees of success. For example, U.S. Pat. No. 4,493,161 and U.S. Pat. No. 229,222 show the uses of visual lures shaped like an animal or plant, respectively. Pheromone attractants have also been used in combination with pesticides. For example, U.S. Pat. No. 4,888,361 to Sonenshine et al. discloses a plastic decoy shaped like a female tick which is impregnated with a sex attraction pheromone, mounting pheromone and a pesticide. In Sonenshine et al., the sex attraction pheromone and mounting pheromone were selected to take advantage of feeding and mating characteristics of many ticks wherein a fed male tick will detach from a host in response to an attraction pheromone and attempt to copulate with a female tick in response to a mounting pheromone.

A problem with using decoys is that they must be specific for the pest to be destroyed. If the ticks to be destroyed do not respond to the decoy which is used, the protection scheme will be ineffective.

Little has been documented of pheromonal regulation of behavior in *Ixodes scapularis* and other Ixodes spp. Pheromones generally affect mate-finding and off-host assembly of ticks. Assembly pheromones induce formation of off-host clusters of various stages and sexes of ticks through arrestment of movement upon contact. Ticks are generally classified as hard ticks or soft ticks, with significant differences between the groups in biology and behavior (such as duration and frequency of feeding and host species). Tick assembly behavior is well characterized from soft ticks (14 species) and attraction occurs in response to aqueous/saline extracts of tick exudate (excreta, feces). Compounds that have been identified from these extracts and eliciting assembly in Argas (soft ticks) include purines or purine-like compounds such as guanine, uric acid, xanthine, and adenine. Behavioral evidence of a water-soluble pheromone inducing assembly has been reported Experientia 33:680–682), *Ixodespersulcatus* (Uspensky, L. V. and O. Y. Emelyanova [1980] "On the existence of pheromone relations in ticks of the genus Ixodes" Zool. Zh. 59:699–704) and *I. ricinus* (Hajkova, C. and M. G. Leahy [1982] "Pheromone-regulated aggregation and larvae, nymphs, and adults of *Ixodes ricinus* L. (Acarina: Ixodidae)" Folia Parasitol. 29:61–67).

Currently there are no pheromone-based methods of control or surveillance (monitoring) for Ixodes ticks. Methods of control against Ixodes ticks (the vectors of Lyme disease, human ehlichiosis and human babesiosis) include use of acaricides (granules and sprays) to reduce tick abundance on lawns and woodland edges, reduction of deer as hosts of ticks, treatment of mice (as tick hosts) with permethrin cyfluthrin, delamethrin, bifentrhin and reduction of tick habitats (vegetation, leaf litter) around houses. Reduction of disease transmission is also obtained through use of repellents on skin and clothing, and timely removal of attached ticks. Acaricides are the primary method used for tick control and those registered for such use include carbaryl, chlorpyrifos, diazinon, cyfluthrin, s-fenvalerate, fluvalinate and permethrin. Repeated and widespread use of these compounds elicits considerable environmental concern (run-off, non-target effects) and cost for area-wide applications.

The combination of acaricide with pheromones has the advantages of enhancing acaricide efficacy by attracting ticks to the acaricide, acting as a species-targeted control method, and the potential for reducing environmental contamination by treating only high risk areas (i.e., backyards, parks, etc.). The concept of combining pheromones with acaricides for tick control has been tested in several successful field trials using extracts of fed males of several species of Amblyonma that produce an aggregation-attachment pheromone (Norval, R. A. I., C. E. Yunker, I. M. Duncan and T. Peter [1991] "Pheromone/acaricidemixtures in the control of the tick *Amblyomma hebraeum*: Effects of acaricides on attraction and attachment" Exp. and Appl. Acarol. 11:233–240). With the subsequent identification of pheromone components, a synthetic pheromone mixture for *Amblyomma hebraeum* and *A. variegatum* (Norval, R. A. I., D. E. Sonenshine, S. A. Allan, M. J. Burridge [1996] "Efficacy of pheromone-acaricide-impregnated tail-tag decoys for controlling the bont tick, *Amblyomma hebraeum* (Acari: Ixodidae), on cattle in Zimbabwe" Exp. Appl. Acarol. 20:31–46) was developed and incorporated, along with acaricide, into a slow-release plastic tag for tick control on cattle. Field trials for control of *A. hebraeum* on cattle in Zimbabwe (Norval el al. [1996] supra) and *A. variegatum* on cattle in Guadeloupe (Allan, S. A., N. Barre, D. E. Sonenshine, and M. J. Burridge [1998] "Efficacy of tags impregnated with pheromone and acaricide for control of *Amblyomma variegalum*" Med. Vet. Entomol. 12:141–150) resulted in high levels of tick control for three months. A patent by Norval et al., 1994 (Attractant decoy for controlling bont tick, U.S. Pat. No. 5,296,227) describes the use of tick pheromone components in conjunction with acaricides, however, these pheromone components do not elicit attraction of *Ixodes scapularis*. The use of the tick pheromone, 2-6-dichlorophenol, considerably enhanced mortality of the American dog tick (*Dermacentor variabilis*) in a study by Sonenshine et al. (Sonenshine, D. D., D. Taylor, and G. Corrigan [1985] "Studies to evaluate the effectiveness of sex pheromone impregnated formulations for control of populations of the American dog tick, *Dermacentor variabilis* (Say) (Acari: Ixodidae)" Exp. Appl . Acarol. 1:23–24), however, this pheromone is not attractive to Ixodes ticks.

BRIEF SUMMARY OF THE INVENTION

The subject invention provides materials and methods useful for tick control. The tick control methods of the subject invention are particularly advantageous because they utilize natural chemical signals (phermones) in combination with an acaricide. The use of environmentally friendly phermones makes it possible to use acaricides in a highly selective and efficient manner thereby reducing exposure of the environment to acaricides.

In a specific embodiment, the subject invention concerns the use of pheromones to control the tick, *Ixodes scapularis*. The pheromones of the subject invention can either attract ticks or cause tick assembly by arresting movement upon contact.

The pheromones of the subject invention can also be used to control other tick species including *Ixodes pacificus* (west coast U.S.), *Ixodes ricinus* (Europe and Asia), *Ixodes persulcatus* (Asia) and *Ixodes holocyclus* (Australia). These Ixodes species are competent vectors of Lyme disease, ehlichiosis, babesiosis and tick-borne encephalitis and also may cause tick paralysis.

DETAILED DISCLOSURE OF THE INVENTION

The subject invention provides materials and methods useful for tick control. In a particularly preferred embodiment, the materials and methods of the subject invention can be used to control *Ixodes scapularis* and related ticks. Specifically exemplified herein is the identification of pheromone compounds which attract and/or cause aggregation of target ticks. The tick control methods of the subject invention are particularly advantageous because they utilize natural chemical signals (phermones) in combination with an acaricide. The use of environmentally friendly phermones makes it possible to use acaricides in a highly selective and efficient manner thereby reducing exposure of the environment to acaricides.

In accordance with the subject invention, a pheromone composition present in cast larval skins of ticks and tick exudate has been found to elicit assembly of nymphs and adults. The results of experiments showing assembly of nymphs is shown in Table 1. The results of experiments showing assembly of adults are shown in Table 2. The response to cast skins is considered due to the deposition of exudates or feces onto the skins before or during the molting process.

TABLE 1

Assembly of *I. scapularis* nymphs in the treatment sector in petri dish bioassays conducted in darkness. Each means represents 10 replicates with 10 nymphs per replicate. Untreated controls consisted of untreated filter paper, larval skins consisted of 10 cast larval skins on filter paper, exposed filter paper was exposed for 30 days after blood-feeding of larvae (10/paper) and the exudate was material scraped from the vial containing the above blood-fed larvae for 30 days.

| | % of *I. scapularis* nymphs in treatment sector (zone 1) (X ± SE) | | | |
|---|---|---|---|---|
| Time | Untreated Control | Larval Skins | Exposed filter paper | Exudate |
| 60 min | 10.0 (4.4) | 36.0 (4.0)** | 40.0 (3.1)** | 30.0 (4.5)** |
| 120 min | 6.0 (3.0) | 34.0 (7.2)** | 38.0 (3.7)** | 24.0 (5.1)** |
| 24 hours | 12.0 (4.4) | 40.0 (7.2)** | 40.0 (2.2)** | 24.0 (5.1)** |

*Significantly different than the untreated control, paired t-test, $P < 0.05$
**Significantly different than the untreated control, paired t-test, $P\ 0.001$

TABLE 2

Assembly of *I. scapularis* adults in response to cast larval skins in the treatment sector in petri dish bioassays. Each mean represents 10 replicates. Untreated sectors consisted of untreated filter paper and larval skin treatments consisted of 10 or 25 cast larval skins placed on filter paper.

| | % of *I. scapularis* adults in the treatment sector (zone I) (X ± SE) | | | | | |
|---|---|---|---|---|---|---|
| | Females | | | Males | | |
| Time | Untreated control | 10 Larval skins | 25 Larval skins | Untreated control | 10 Larval skins | 25 Larval skins |
| 1 hour | 10.0 (10.0) | 10.0 (10.0) | 50.0 (16.6)* | 6.0 (6.0) | 20.0 (13.3) | 30.0 (15.0) |
| 2 hours | 6.0 (6.0) | 10.0 (10.0) | 60.0 (16.3)** | 6.0 (6.0) | 10.0 (10.0) | 40.0 (16.0)* |
| 24 hours | 10.0 (10./0) | 10.0 (10.0) | 70.0 (15.3)** | 6.0 (6.0) | 10.0 (10.0) | 40.0 (16.0)* |

*Significantly different than the untreated control, paired t-test, $P < 0.05$
**Significantly different than the untreated control, paired t-test, $P < 0.01$ A further aspect of the subject invention is the discovery of significant assembly of both nymphs and adults to purines and purine-like compounds. Assembly of nymphs to these compounds is shown in Table 3. Assembly of adults to these compounds is shown in Table 4.

TABLE 3

Assembly of *I. scapularis* nymphs in the treatment sector in petri dish bioassays conducted in darkness. Each means represents 10 replicates with 10 nymphs per replicate. Untreated controls consisted of untreated filter paper and standards consisted of 0.5 mg deposited onto the filter paper.

| | % of *I. scapularis* nymphs in treatment sector (zone 1) (X ± SE) | | | | | | | | |
|---|---|---|---|---|---|---|---|---|---|
| | Time | Guanine | Uric Acid | Hypoxanthine | Xanthine | Inosine | Adenine | Hematin | Mixture[a] |
| 60 min | 10.0 (4.4) | 16.0 (5.0) | 20.0 (5.1) | 26.0 (5.1)** | 22.0 (2.0)** | 26.0 (4.0)** | 6.5 (4.1) | 24.0 (4.0)* | 16.0 (6.4) |
| 120 min | 6.0 (3.0) | 20.0 (4.8)* | 30.0 (8.5)** | 24.0 (5.6)* | 28.0 (4.8)** | 26.0 (2.4)** | 16.0 (7.5) | 24.0 (6.7)** | 14.0 (7.4) |
| 24 hours | 12.0 (4.4) | 20.0 (5.0) | 24.0 (6.0) | 18.0 (6.6) | 32.0 (3.7)** | 36.0 (6.1)** | 14.0 (4.1) | 26.0 (5.6)* | 14.0 (3.7) |

TABLE 3-continued

Assembly of *I. scapularis* nymphs in the treatment sector in petri dish bioassays conducted in darkness. Each means represents 10 replicates with 10 nymphs per replicate. Untreated controls consisted of untreated filter paper and standards consisted of 0.5 mg deposited onto the filter paper.

% of *I. scapularis* nymphs in treatment sector (zone 1) (X ± SE)

| Time | Guanine | Uric Acid | Hypoxanthine | Xanthine | Inosine | Adenine | Hematin | Mixture[a] |
|------|---------|-----------|--------------|----------|---------|---------|---------|------------|

[a]Mixture consists of guanine, xanthine and adenine in a 25:1:1 ratio and was based on an attractive mixture for *Argas peralcus* (Dusbabek et al., 1991, Exp. Appl. Acarol. 11:307–316).
*Significantly different than the untreated control, paired t-test, P < 0.05
**Significantly different than the untreated control, P < 0.001

TABLE 4

Assembly of *I. scapularis* adults to purine compounds in the treatment sector of a petri dish. Each mean represents 15 replicates. Untreated consisted of untreated filter paper and 0.5 mg of standards with deposited on each treatment.

% of *I. scapilaris* adults in the treatment sector (zone I) (X ± SE)

| | Females | | | | Males | | | |
|---|---|---|---|---|---|---|---|---|
| Time | Untreated | Guanine | Inosine | Xanthine | Untreated | Guanine | Inosine | Xanthine |
| 1 hour | 10.0 (10.0) | 33.3 (12.6) | 40.0 (13.1)* | 33.3 (12.6) | 6.0 (6.0) | 33.3 (12.6)* | 40.0 (13.1)* | 26.6 (11.8) |
| 2 hours | 6.0 (6.0) | 33.3 (12.6)* | 26.6 (11.8) | 33.3 (12.6)* | 6.0 (6.0) | 40.0 (12.6)* | 46.6 (13.3)* | 33.3 (12.6)* |
| 24 hours | 10.0 (10.0) | 40.0 (16.4)* | 20.0 (13.3) | 40.0 (16.4)* | 6.0 (6.0) | 60.0 (16.4)** | 40. (16.4)* | 40.0 (16.0)* |

*Significantly different than the untreated control, paired t-test, P < 0.05
**Significantly different than the untreated control, paired t-test, P < 0.001

The subject invention provides compounds which attract and/or cause assembly in Ixodes ticks. More specifically, these compounds cause ticks to move towards and/or stay in contact with the compound once the ticks have encountered the compound. Compounds which are specifically exemplified herein include hypoxanthine, xanthine, inosine, adenine, hematin and other compounds from exudate or cast skins. Advantageously, these compounds have been found to offset the behavior of nymphs as well as males and females. The chemical(s) affect behavior of nymphs as well as males and females. The chemical(s) may be present in a single point source in mutiple point sources (such as granules), or as a liquid or fine powder. The chemical(s) may be present as a spray, granular form, encapsulated, single-point source delivery system or applied onto an acaricide-delivering technology. The chemical (s) may be applied alone or in association with an acaricide or biological control agent. The chemical(s) may attract or cause assembly in *Ixodes scapularis* ticks as well as other Ixodes including *Ixodes holocyclus, Ixodes persulcatus, Ixodes ricinus* and *Ixodes pacificus* and others. The chemical(s) are used for the purpose of tick control or surveillance. The chemical(s) are based on natural chemicals present in tick excreta or cast skins. The biological control agent may be, for example, a fungus, such as *Beuvaria bassiana*, or a bacterium such as *Bacillus thuringiensis*.

The identification of pheromones in *Ixodes scapularis* provides the basis for a control strategy for reduction of *I. scapularis* and other disease-carrying ticks. The control methods of the subject invention provide clear advantages over current control strategies. Pheromones can be combined with one or more acaricides in appropriate formulations to be placed in areas where human-tick and/or animal-tick interaction is greatest. For instance, application of a pheromone/acaricidemixture to vegetation along frequently used pathways can be used to attract and/or arrest movement of ticks in the acaricide-treated areas and reduce exposure of people using the path to questing ticks. The pheromone mixture can also be used in conjunction with biological control agents or alone.

Additionally, incorporation of pheromones into insecticide collars on dogs or other controlled-release devices can be used to attract ticks towards the pheromone source and areas with high levels of acaricide.

Advantages of pheromone/acaricidecontrol strategies include species-specificity,and with selected treatment of high risk areas (i.e., edges of paths, lawns) reduces overall acaricide used for treatment. An effective assembly pheromone (resulting in arrestment of movement) can be combined with low levels of acaricide to produce effective control with reduced acaricide levels, or with biocontrol agents such as fungal pathogens to effectively treat questing ticks. In addition, surveillance of ticks currently entails dragging a cloth over vegetation and counting ticks on the cloth. This method exposes the collector to high tick exposure and the method varies in efficiency considerably with the collector. Use of an assembly pheromone in a trap allows for reduced exposure to potentially infected ticks and provides a less-biased sampling method.

The same pheromone components produced by *I. scapularis* may also be effective against other Ixodes species important as disease vectors.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for the control of Ixodes ticks, which comprises administering to said ticks or their situs a composition comprising a fungal biocontrol agent that kills ticks and a chemical from tick excreta which causes ticks to aggregate wherein said aggregation chemical is applied prior to, or contemporaneous with, the application of said biocontrol agent so as to cause ticks to aggregate at the situs of said control agent, wherein said biocontrol agent is *Beauvaria bassiana*.

* * * * *

UNITED STATES PATENT AND TRADEMARK OFFICE
CERTIFICATE OF CORRECTION

PATENT NO. : 6,331,297 B1
DATED : December 18, 2001
INVENTOR(S) : Sandra Anne Allan, Daniel E. Sonenshine and Michael John Burridge It is certified that error appears in the above-identified patent and that said Letters Patent is hereby corrected as shown below:

Column 1,
Line 64, "reported Experientia" should read -- reported from *Ixodes holocyclus* (Treverrow, N.L., B.F. Stone, M. Cowie [1977] "Aggregation pheromones in 2 Australian hard ticks, *Ixodes holocyclus* and *Aponomma concolor*" Experientia --.
Line 65, "*Ixodespersulcatus*" should read -- *Ixodes persulcatus* --.

Column 2,
Line 34, "Amblyonma" should read -- Amblyomma --.
Line 55, "*variegalum*" should read -- *variegatum* --.

Columns 3-4,
Table 3, "treatment sector (zone 1) (X±SE)" should be entirely underlined and read -- treatment sector (zone 1)(X±SE) --.

Columns 5-6,
Table 3, "treatment sector (zone 1) (X±SE)" should be entirely underlined and read -- treatment sector (zone 1)(X±SE) --.

Column 5,
Table 4, "*I. scapilaris*" should read -- *I. scapularis* --.

Signed and Sealed this

Thirtieth Day of April, 2002

*Attest:*

*Attesting Officer*

JAMES E. ROGAN
*Director of the United States Patent and Trademark Office*